United States Patent [19]

Muller-Eberhard et al.

[11] Patent Number: 4,661,347

[45] Date of Patent: Apr. 28, 1987

[54] CYTOTOXIC COMPOSITIONS

[75] Inventors: Hans J. Muller-Eberhard; Carl-Wilhelm E. Vogel, both of LaJolla, Calif.

[73] Assignee: Scripps Clinic, LaJolla, Calif.

[21] Appl. No.: 709,007

[22] Filed: Mar. 7, 1985

Related U.S. Application Data

[63] Continuation of Ser. No. 441,135, Nov. 12, 1982, abandoned.

[51] Int. Cl.$^4$ .................. A61K 39/00; C07K 17/06
[52] U.S. Cl. ............................ 424/85; 424/98; 530/387; 530/389; 530/390; 530/395; 530/402; 530/403; 530/404; 530/408
[58] Field of Search .................. 424/85, 98; 436/548; 260/112 R

[56] References Cited

PUBLICATIONS

Vogel et al, *PNAS*, 78(12), pp. 7707–7711, 12/81.
Thorpe et al., Eur. J. Biochem., 116, 447–454 (1981).
Derwent Abstract No. 55398 (European Patent Office Application No. 55115)—Teijin K. K.
Derwent Abstract No. 57670 (European Patent Office Application No. 55575)—Teijin K. K.
Ghose et al., J. Natl. Cancer Inst., 61, 657–676, (1978).
Gilliland et al., Proc. Natl. Acad. Sci., USA 77, 4539–4543 (1980).
Krolick et al., Proc. Natl. Aca. Sci., USA 77, 5419–5423 (1980).

Primary Examiner—Morton Foelak
Assistant Examiner—Garnette D. Draper
Attorney, Agent, or Firm—William C. Martens; Leroy Whitaker

[57] ABSTRACT

A cytotoxic composition is described comprising a moiety having binding affinity to a surface structure of a cell and coupled to a moiety having activity as a structural subunit of C3/C5 convertase.

4 Claims, No Drawings

CYTOTOXIC COMPOSITIONS

This application is a continuaion of application Ser. No. 441,135, filed Nov. 12, 1982 now abandoned.

BACKGROUND OF THE INVENTION

Attempts have been made over the last several years to use antibodies in combination with cytotoxic agents, thereby seeking to effect selective action on target cells and to prevent or minimize the otherwise non-specific effect of cytotoxic agents. A review of the use of antibody-linked cytotoxic agents is provided in Ghose et al., *J. Natl. Cancer Inst.* 61, 657–676 (1978). As described in that publication, the methods of using a combination of antibodies and cytotoxic agents have ranged from covalent bonding using linkage-providing molecules, non-covalent binding, and simple mixing (see Table 1 of Ghose et al.).

With the advent of hybridoma technology and the accompanying availability of monoclonal antibodies, the feasibility of the antibody-cytotoxic agent approach has brightened considerably due to the ability potentially to precisely direct the complex to the intended target cell population.

To date, the concept of using antibodies in conjunction with biologically active agents has been limited to those agents which have inherent and nonspecific cytotoxic activity, and the degree of specificity has been dependent upon the limiting effect, if any, imposed by the accompanying antibody. Thus, a variety of recognized cytotoxic agents, including, for example, diphtheria toxin [Gilliland et al., *Proc. Natl. Acad. Sci. USA* 77, 4539–4543 (1980)]; ricin [Krolick et al., *Proc. Natl. Aca. Sci. USA* 77, 5419–5423 (1980)]; subunit A of ricin (U.S. Pat. No. 4,350,626); and gelonin [Thorpe et al., *Eur. J. Biochem.* 116, 447–454 (1981)], have been covalently coupled to antibody molecules.

This approach, of course, suffers from certain limitations. First, as noted, the agent carries inherent and indiscriminate cytotoxic activity. Subject to whatever degree of cell-directing specificity the antibody may provide, the cytotoxic agent may otherwise indiscriminately attack any cell it can approach. Secondly, although the activity of the cytotoxic agent is indiscriminate, it is dependent upon and limited by the ability of the agent to become internalized by the target cell.

In view of these limitations, it appeared ideal to seek to develop a conjugate, the action of which is not dependent upon an agent's innate and indiscriminate cytotoxic properties, but which instead is capable, in conjunction with the cell-fixing properties of the antibody, of utilizing one of the host's own cytotoxic mechanisms, namely, complement. This approach circumvents non-specific toxicity and avoids the need for internalization by the target cells of the cytotoxic agent.

It is to such a composition that this invention is directed. Briefly, this invention is directed to a composition comprising a molecule having binding affinity to a surface structure of a cell and a molecule having activity as a structural subunit of the stable and control resistant C3/C5 convertase. A preferred composition of this invention is one comprising an antibody directed to a cell surface constituent and coupled to cobra venom factor (CVF).

Cobra venom factor (CVF) is a glycoprotein having a molecular weight of about 140,000 present in the venom of the cobra *Naja naja.* CVF is the structural subunit of a C3/C5 convertase of the alternative complement pathway. It appears to be immunochemically [Alper et al., *Science* 191, 1275–1276 (1976)] and structurally [Vogel et al., *Fed. Proc. Fed. Am. Soc. Exp. Biol.* 40, 1020 (abst.) (1981)] related to human C3 and C3b. CVF exhibits a C3b-like function when added to mammalian serum in that, together with factor B and in the presence of factor D and $Mg^{++}$, it forms a soluble C3/C5 convertase (CVF,Bb) that efficiently initiates assembly of the membrane attack complex (MAC) of complement.

Although CVF exhibits the above actions, it is not cytotoxic per se. Instead, it has been shown, upon injection into rabbits, that CVF, upon complexing with a plasma constituent, leads to inactivation and depletion of C3 [Cochrane et al., *J. Immunol.* 105, 55–69 (1970); see also, Vogt et al., *Hoppe-Seyler's Z. Physiol. Chem.* 355, 171–183 (1974)]. However, when coupled with an antibody directed to a cell surface constituent, the complement-activating action of CVF is effective in activating the host's own cytotoxic complement mechanisms specifically against the antibody target cell.

SUMMARY OF THE INVENTION

Therefore, this invention is directed to a composition comprising a moiety having binding affinity to a surface structure of a cell and coupled to a moiety having activity as a structural subunit of C3/C5 convertase.

A preferred composition of this invention comprises an antibody or a fragment thereof directed to a cell surface constituent and coupled to cobra venom factor.

DETAILED DESCRIPTION OF THE INVENTION

As described above, this invention is directed to compositions useful in activating host cytotoxic mechanisms toward specific cellular targets. As also noted, CVF, a preferred constituent of the compositions of this invention, is similar to human C3 and C3b of complement. The compositions of this invention comprise two active moieties covalently joined, preferably via a coupling agent. One of the active moieties is represented by a molecule having binding affinity to a surface structure of a target cell. Typical such molecules are, for example, hormones, lectins, growth factors, antibodies, and the like. The molecules of choice are antibodies or fragments thereof having cell surface binding affinity.

Although monoclonal antibodies are preferred, they are not essential. Immunoglobulin fractions from serum can be used. However, since the immunoglobulin fraction of an antiserum contains a multitude of antibodies directed to a wide range of divergent antigens, a practical usefulness of the compositions of this invention dictates the need to isolate a desired collection of antibiodies, each directed to a surface antigen present on the particular target cell.

An effective collection of such antibodies can be obtained by passing the immunoglobulin fraction over a column containing the respective antigen chemically coupled to a matrix. Antibody specific to the antigen will be retained on the column while unrelated immunoglobulin passes through. The retained antibody then can be collected by elution from the column using suitable eluting agents, for example, acidic buffers or chaotropic agents. It should be noted that the isolated immunoglobulin, although directed to a single antigen, is not homogeneous. It comprises antibodies directed to a variety of antigenic determinants present on the antigen molecule.

As a result, the possibility exists for cross-reaction with other related antigens.

It is highly preferred, therefore, to use monoclonal antibodies in preparing the compositions of this invention since they are directed to only one of possibly many antigenic determinants present on an antigen. Monoclonal antibodies are available by recognized methodology from hybridomas derived from lymphocytes from spleen or other organs.

The immunoglobulins used in producing the composition of this invention, whether monoclonal or not, can be from any Ig class, i.e., IgG, IgA, IgM, IgD, and IgE. Moreover, antigen-binding fragments of Ig, e.g., Fab or Fab'$_2$, can be used in producing compositions of this invention.

A second moiety of the compositions of this invention is one which serves as a structural subunit of C3/C5 convertase. Molecules suitable for use as such moieties are cobra venom factor (CVF), peptides derived from CVF, appropriately modified stable human C3b, peptides derived from human C3b, or synthetic peptides exhibiting structural subunit activity for C3/C5 convertase. Preferably, the molecule of choice for this moiety is cobra venom factor.

Lyophilized cobra venom is available from a variety of commercial suppliers. Cobra venom factor can be isolated from cobra venom by sequential column chromatography according to established procedures [see, e.g., Ballow, M. and Cochrane, C. G., *J. Immunol.* 103, 944-952 (1969)].

As noted from the foregoing discussion, the compositions of this invention comprise at least two separate active moieties, one of which affords cell surface binding affinity (CSB) and the other of which acts as a C3/C5 convertase (Conv). These are joined in the compositions of this invention through a coupling reagent, the requirements of the resulting composition being (a) the presence of at least one of each class of moiety, and (b) the retention of the innate binding or enzymatic activity of at least one of each class of moiety.

In accordance with the above limitations, the compositions of this invention can be dimeric (CSB-Conv) i.e., contain one of each class of moiety; trimeric [(CSB$_2$-Conv) or (CSB-Conv$_2$)], i.e., contain two of one class of moiety and one of the other; tetrameric [(CSB$_3$-Conv), (CSB$_2$-Conv$_2$), or CSB-Conv$_3$)]; and the like. Compositions of choice appear to be dimeric or tetrameric, and most preferably, tetrameric.

Highly preferred compositions of this invention are those in which the CSB moiety is antibody, preferably monoclonal antibody, or an antigen binding fragment of antibody, and the Conv moiety is cobra venom factor. Typical such compositions are Ab-CVF, Ab$_2$-CVF, Ab-CVF$_2$, Ab$_3$-CVF, Ab$_2$-CVF$_2$, Ab-CVF$_3$, and the like.

As previously noted, by reason of the conjugation of CVF to antibody, the CVF complement-activation mechanism and accompanying cytotoxic effect have been transferred to the surface of the target cells to which the antibody is specific. As further previously mentioned, this cytotoxic effect does not occur upon administration of CVF alone.

Although the highly preferred CVF is similar to human C3 and C3b, and the convertase CVF,Bb is closely related to the physiological enzyme C3b,Bb, the former enzyme differs from the latter in several important respects. First, whereas the half-life of C3b,Bb at 37° C. is 1.5 min., that of CVF,Bb is 7 hours. Secondly, C3b,Bb is inactivated by factor H, and C3b is degraded and inactivated by the combined action of factors H and I; in contrast, CVF and the enzyme CVF,Bb are entirely resistant to the action of these complement control proteins. Thirdly, C3b,Bb requires additional C3b in order to be able to act on C5; CVF,Bb can activate C5 directly and thus can initiate membrane attack complex formation without C3. Fourthly, whereas nascent or metastable C3b can attach itself firmly to targets of complement attack, CVF lacks such binding ability; its effect arises via the binding ability and cell-directing effect of the conjugate antibody.

Thus, what we have particularly discovered and what is herein particularly claimed is a synthetic antibody-CVF complex that serves as an activator of a specific cytolytic alternative complement pathway. It is independent of the initial enzyme of either the classical complement pathway (C1) or the alternative complement pathway [C3(H$_2$O),Bb], and it is not subject to control by factors H and I.

In preparing the compositions of this invention, the CSB and Conv moieties are joined via a suitable coupling reagent. A wide variety of coupling agents is reported in Ghose, T., and Blair, A. H., *J. Natl. Cancer Inst.* 61, 657-676 (1980). This paper reports, in coupling antibody to cytotoxic agents, the use of carbodiimides as well as other bifunctional reagents, such as glutaraldehyde, p-benzoquinone, p,p'-difluoro-m,m'-dinitrodiphenylsulfone, dimethyl adipimidate, and the like. Since it is highly desirable to preclude formation of homopolymers, e.g., (CSB)$_n$ or (Conv)$_n$, it is preferred to use a heterobifunctional reagent, thereby ensuring formation of compositions having at least one of each class of moiety, i.e., those of this invention, with prevention of the formation, even in part, of homopolymers. Examples of such heterobifunctional reagents are N-succinimidyl-3-(2-pyridyldithio)propionate (SPDP), m-maleimidobenzoyl-N-hydroxysuccinimidyl ester, bromoacetyl-p-aminobenzoyl-N-hydroxysuccinimidyl ester, iodoacetyl-N-hydroxysuccinimidyl ester, and the like.

As an example, using SPDP as coupling agent, a composition of this invention containing Ab and CVF can be prepared by (a) separately modifying both Ab and CVF by reaction with SPDP, (b) reducing the Ab-containing product, (c) causing formation of the composition by mixing the Ab-containing and CVF-containing products, and (d) separating non-reacted monomers by gel filtration.

The compositions of this invention have general applicability to the specific and selective killing of a cell type defined by particular antigenic markers. As such, they are useful, for example, in the immunotherapy of cancer, for treating parasitic infections, and for treating a wide range of autoimmune diseases. Moreover, the compositions have several in vitro applications, including, for example, tissue typing assays; elimination of leukemic cells in bone marrow prior to autologous bone marrow transplantation; elimination of T-cells in bone marrow prior to allogeneic bone marrow transplantation; and killing of wild types for selection of mutants.

The compositions of this invention can be used in a variety of pharmaceutical compositions and formulations and can be administered by a variety of conventional routes, such as intramuscular, intravenous, subcutaneous, and intraperitoneal.

In administering the compositions of this invention parenterally or intraperitoneally, the pharmaceutical forms suitable for injection include sterile aqueous solutions or dispersions and sterile powders for reconstitution into sterile injectible solutions or dispersions. The carrier can be a solvent or dispersing medium containing, for example, water, ethanol, polyol (for example glycerol, propylene glycol, liquid polyethylene glycol, and the like), suitable mixtures thereof, and vegetable oils. Proper fluidity can be maintained, for example, by the use of a coating such as lecithin, by the maintenance of the required particle size in the case of dispersion and by the use of surfactants. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin.

Sterile injectable solutions can be prepared by incorporating the compositions of this invention in the required amount of the appropriate solvent with various of the other ingredients, as desired.

If desired, and for more effective distribution, the compositions can be incorporated into slow release systems such as polymer matrices, liposomes, and microspheres. Moreover, the compositions of this invention can be administered either alone or as a mixture of a plurality of active ingredients.

Doses of the compositions of this invention are administered to the recipient for a period during which a therapeutic response is desired. The weight of the recipient and mode of administration will have an influence upon the size of the dose necessary to induce a particular response. Generally, for parenteral or intraperitoneal administration, the dose will be chosen to maintain functional complement levels. Complement levels can be easily determined by a hemolytic assay. Simultaneous injection of plasma as an additional source of complement may be helpful. Based on animal studies on the effect of CVF on the complement levels, one would suggest that the dose will not exceed 2 mg of complex per kg of body weight.

It is especially advantageous to formulate the compositions of this invention in unit dosage form for ease of administration and uniformity of dosage. Unit dosage form as used herein refers to a physically discrete unit suited as unitary dosages for the subject to be treated. Each unit contains a predetermined quantity of the composition calculated to produce the desired therapeutic effect in association with the pharmaceutically acceptable carrier. The specific unit dosage form is dictated by and directly dependent upon (a) the unique characteristics of the particular composition and (b) the particular therapeutic effect to be achieved.

The following examples are illustrative of this invention. They are not intended to be limiting upon the scope thereof.

Example 1—Preparation of
2-Pyridyldithiopropionylated Cobra Venom Factor

To 2.5 ml. of buffer A (0.1 M sodium phosphate, 0.1 M NaCl, pH 7.5) containing 3.5 mg. of purified CVF a 20 mM solution of N-succinimidyl-3-(2-pyridyldithio)-propionate (SPDP) in absolute ethanol was added in an amount representing a 5.5 molar excess of SPDP relative to the CVF. The mixture was stirred for 30 minutes at room temperature.

The 2-pyridyldithiopropionylated CVF product was separated from the reaction by-product, N-hydroxysuccinimide, and excess SPDP by gel filtration on a Sephadex G-25 column (1.5 cm.×5 cm.) which had been equilibrated with buffer A. (The amount of SPDP that is used determines the degree of substitution with 2-pyridyldithiopropionyl group. Using from about 3-fold to about 7-fold molar excess of SPDP provides from about 1.5 to about 4 2-pyridyldithiopropionyl groups per CVF.)

Example 2—Preparation of
2-Pyridyldithiopropionylated Monoclonal Antibody

Employing the method of Example 1, 6.9 mg. of purified monoclonal IgG2a hybridoma antibody 9.2.27 to a human melanoma-associated antigen (250,000 dalton glycoprotein) [Morgan, A. C., Galloway, D. R., and Reisfeld, R. A., *Hybridoma* 1, 27 (1981)] were converted to 2-pvridyldithiopropionylated monoclonal antibody. The product was separated from N-hydroxysuccinimide and excess SPDP as in Example 1 over Sephadex G-25 which had been equilbrated with buffer B (0.1M sodium acetate, 0.1M NaCl, pH 4.5).

Example 3—Preparation of Thiolated Monoclonal Antibody

To 4.4 mg. of the 2-pyridyldithiopropionylated monoclonal antibody from Example 2 dissolved in 1.5 ml. of buffer B were added a 500 mM solution of dithiothreitol (DTT) in buffer B in an amount to provide a 45 mM DDT final concentration. The resulting mixture was maintained at room temperature for 20 minutes with occasional stirring. The released pyridine-2-thione and excess DTT was removed by gel filtration over Sephadex G-25 using buffer A as eluant. The resulting product, thiolated monoclonal antibody, is used without delay in the following preparation of the antibody - CVF complex in order to avoid spontaneous oxidation of the product to disulfide-linked antibody polymer.

Example 4—Preparation of Monoclonal Antibody - CVF Complex

Equimolar amounts (approximately 15 nM each) of the products from Examples 1 and 3 were mixed in a total volume of 3 ml. of buffer A to a final protein concentration of 1.6 mg./ml. The mixture was incubated at room temperature with occasional stirring for about 21 hours. The course of the reaction was monitored at 343 nm. for release of pyridine-2-thione. The mixture then was filtered at 4° C. on a column (1.6 cm.×56 cm.) of Ultrogel AcA 22. Fractions of 1.2 ml. each were collected at a linear flow rate of 2 cm./hour to separate released pyridine-2-thione, unreacted antibody, and unreacted CVF from the disulfide-linked complex of antibody and CVF. The formal ccmplexes consisted of dimeric, trimeric, and tetrameric compositions.

Other Compositions

Using the methods described in the foregoing examples, complexes ccmprising CVF and the following antibodies were also prepared:

(a) $R_{24}$ to human melanoma cells (depicts the $G_{D3}$ ganglioside) [Pukel, C. S., Lloyd, K. O., Travassos, L. R., Dippold, W. G., Oettgen, H. F., and Old, L. J., *J. Exp. Med.* 155, 1133–1147 (1982)].

(b) SC1 to human T-cells (for bone marrow transplantations) [Fox, R. I., Fong, S., Sabharwal, N., Carstens, S. A., Kung, P. C., and Vaughan, J. H., *J. Immunol.* 128, 351-354 (1982)].

(c) T305 to human leukemia cells [Fox, R., McMillan, R., Spruce, W., Tani, P., and Mason, D., and The Scripps Clinic Bone Marrow Transplantation Team, *Blood* 60, 578-582 (1982)].

(d) 123 to human parasite *Entomoeba histolytica* [Lopez, J. S., Jensen, F. J., Ximenez, C., and Ortiz-Ortiz, L., *Fed. Proc. Fed. Am. Soc. Exp. Biol.* 41, 484 (1982)].

Biological Activity of the Complex

The cytotoxic activity of the complexes of this invention was determined by a $^{51}Cr$ release assay. In this assay, approximately $5 \times 10^6$ antigen-positive target cells (M21 human melanoma cells) were labeled with 200 $\mu$Ci of $Na_2{}^{51}CrO_4$ by incubation for 1 hour at 37° C. in a humidified chamber containing 5% $CO_2$/95% air. Cells were subsequently washed and subjected to a second hour of incubation to release loosely bound $^{51}Cr$. The cells were then adjusted to approximately $1 \times 10^5$ cells/ml which corresponds to approximately 5,000 cpm/50 $\mu$l of cell suspension. Duplicate 50 $\mu$l cell suspension samples were incubated for 30 min. at 37° C. with 50 $\mu$l of the monoclonal antibody-CVF complex of Example 4 at approximately 0.1 mg/ml protein concentration. Subsequently, the cells were sedimented by centrifugation, and the supernatant was discarded. Guinea pig serum (150 $\mu$l) was added, and the cell suspension was incubated for 5 hours at 37° C. in a humidified chamber with 5% $CO_2$/95% air. The reaction was stopped by adding 700 $\mu$l of cold buffer (10 mM sodium phosphate, 140 mM sodium chloride, 0.5% bovine serum albumin, pH 7.5), vortexing and centrifugation. An aliquot of the supernatant was assayed for radioactivity. Specific $^{51}Cr$ release was calculated using the standard formula $$\frac{100 \times (\text{experimental cpm} - \text{spontaneous cpm})}{(\text{maximal cpm} - \text{spontaneous cpm})}$$

Specific $^{51}Cr$ release from the target cells reached 65% within 5 hours. A 5 $\mu$g dose of the complex was at least as efficient in killing the melanoma cells as 50 $\mu$l of a polycolonal unadsorbed antiserum raised against whole melanoma cells. In contrast, the unconjugated monoclonal antibody tested in amounts of 2.5 to 100 $\mu$g showed no killing activity. CVF tested by itself in amounts of 2.5 to 35 $\mu$g or a mixture of CVF and monoclonal antibody in the presence of serum was inactive.

The effect of the treatment of the human melanoma cells with the monoclonal antibody-CVF complexes of Example 4 and complement was also morphologically characterized by scanning electron microscopy. Treated cells exhibited typical morphological changes, i.e., the number of surface protrusions decreased, clusters of erosions appeared, occasionally large membrane blebs were seen, and total membrane disintegration occurred.

We claim:

1. A composition comprising a monoclonal antibody having binding affinity to a surface structure of a cell and coupled to a moiety having activity as a structural subunit of C3/C5 convertase.

2. Composition of claim 1, in which the moiety having activity as a structural subunit of C3/C5 convertase is cobra venom factor or an active fragment thereof.

3. Composition of claim 2, in which the moieties are covalently joined using N-succinimidyl-3-(2-pyridyldithio)propionate as coupling agent.

4. Composition of claim 3, in which the average total number of coupled moieties is about 4 or less.

* * * * *

UNITED STATES PATENT AND TRADEMARK OFFICE
CERTIFICATE OF CORRECTION

PATENT NO. : 4,661,347
DATED : 4/28/87
INVENTOR(S) : Muller-Eberhard, et al.

It is certified that error appears in the above-identified patent and that said Letters Patent is hereby corrected as shown below:

In Column 1, line 6, please insert:

-- This invention was made with government support under Grant Nos. AI 17354 and CA 27489 awarded by the National Institutes of Health. The government has certain rights in the invention. --

Signed and Sealed this

Twenty-second Day of March, 1994

Attest:

BRUCE LEHMAN

Attesting Officer     Commissioner of Patents and Trademarks